US00PP33168P3

(12) United States Plant Patent
Hansoti

(10) Patent No.: US PP33,168 P3
(45) Date of Patent: Jun. 15, 2021

(54) ***SANSEVIERIA* PLANT NAMED 'HANSOTI21'**

(50) Latin Name: *Sansevieria trifasciata*
Varietal Denomination: HANSOTI21

(71) Applicant: Ashish Hansoti, Mumbai (IN)

(72) Inventor: Ashish Hansoti, Mumbai (IN)

( * ) Notice: Subject to any disclaimer, the term of this patent is extended or adjusted under 35 U.S.C. 154(b) by 0 days.

(21) Appl. No.: 17/010,250

(22) Filed: Sep. 2, 2020

(65) Prior Publication Data

US 2021/0068326 P1 Mar. 4, 2021

(30) Foreign Application Priority Data

Sep. 4, 2019 (QZ) ..... PBR 2019/2153

(51) Int. Cl.
*A01H 5/12* (2018.01)
*A01H 6/12* (2018.01)

(52) U.S. Cl.
USPC ..... Plt./382
CPC ..... *A01H 6/12* (2018.05)

(58) Field of Classification Search
USPC ..... Plt./382
CPC ..... A01H 6/12; A01H 5/12
See application file for complete search history.

*Primary Examiner* — Keith O. Robinson
(74) *Attorney, Agent, or Firm* — Cassandra Bright

(57) ABSTRACT

A new and distinct cultivar of *Sansevieria* plant named 'HANSOTI21' is disclosed, characterized by unusual twisted, curled, compact foliage arranged in flattened, spiral rosettes. The new cultivar is a compact Birds Nest type *Sansevieria* forming small plants, reaching only about 12 cm in height at maturity. Plants require little water, having a moderate tolerance for drought, and are also tolerant of very wet conditions. Foliage is green and yellow-green banded with a yellow margin. The new variety is a *Sansevieria*, typically produced as an indoor ornamental plant.

6 Drawing Sheets

Latin name of the genus and species: *Sansevieria trifasciata.*

Variety denomination: 'HANSOTI21'.

BACKGROUND OF THE INVENTION

The present invention relates to a new and distinct cultivar of *Sansevieria* plant, botanically known as *Sansevieria trifasciata*, of the family Asparagaceae, hereinafter referred to by the cultivar name 'HANSOTI21'.

*Sansevieria* is a monocotyledonous plant with fleshy, succulent leaves which are available in a huge range of species, varieties and cultivars as an outdoor ornamental plant (under tropical conditions) or as indoor plants.

The new *Sansevieria* 'HANSOTI21' was discovered and selected by the inventor, Ashish Hansoti, as a naturally occurring, single whole plant mutation within a planting of *Sansevieria trifasciata* 'Hahnii Green Compacta', a non-patented Hahnii or Birds Nest type of *Sansevieria*. The discovery was made at the inventor's nursery, in Village Vangani, District Thane, Maharashtra State in Western India. The inventor noted the unique plant had particularly compact growth and wide leaves compared to the normal, common green *Sansevieria trifasciata* 'Hahnii' types. 'HANSOTI21' originated as a naturally-occurring mutation of the *Sansevieria* variety 'Hahnii Green Compacta' (unpatented) selected in May 2011.

Asexual reproduction of the new *Sansevieria* cultivar by vegetative cuttings was first performed in August of 2011 at a commercial nursery in Village Vangani, District Thane, Maharashtra State in Western India. This first and subsequent propagation have shown that the distinctive combination of characteristics of the new cultivar are reproduced true to type as long as the propagation was done through side shoots (basal suckers) originating from the base of the originally discovered plant. Thus, it can be said that the new cultivar reproduces true to type through side shoots (basal suckers).

BRIEF SUMMARY OF THE INVENTION

The following traits have been repeatedly observed and are determined to be unique characteristics of 'HANSOTI21', which in combination distinguish this *Sansevieria* as a new and distinct cultivar:

1. Twisted, curved and compact foliage with a very horizontal, flat spiral presentation of the whole rosette. This "leaf vortex" may be twisted clockwise or anti-clockwise in individual plants.
2. 9-10 cm total plant height (measured from pot rim) in a ready to sell plant with 8-9 leaves in a 12 cm pot and 10-12 cm in older, mature plants with 15-17 leaves grown in a 15 cm pots. This vertically compact or flat presentation and the intense twisting of the leaves is characteristic of this variety. Total plant width of these older, mature plants is 18-21 cm so as to form a flattened disc of twisted, variegated, tough *Sansevieria* leaves.

'HANSOTI21' coloration is otherwise similar to many *Sansevieria trifasciata* cultivars including *Sansevieria trifasciata* 'Future Superba' and the old, tall *Sansevieria trifasciata* 'Laurentii'. Variegated foliage with a wide green band in centre and creamy yellow border of 3-15 mm wide, the whole marked with horizontal and alternate bands or striations of light and dark green across the leaf blade as is typical with a lot of the *Sansevieria trifasciata* varieties.

Leaf width in all *Sansevieria trifasciata* cultivars is quite variable, depending on growing conditions and overall feed levels as well as ratios of Potassium, Nitrogen and Phosphorus and the strongest, healthiest plants have the widest leaves. This variation means leaf width in 'Hansoti21' can be anything from 3 cm to 6 cm wide depending on season, growing conditions and plant vigour. Typically, the leaves are of medium width (4 cm average measured at the widest part of the mature leaf under good growing conditions) and lanceolate with a firm, waxy texture. The blades are thick or fleshy, curved and twisted.

The new variety 'HANSOTI21' can be considered a variety of *Sansevieria* in the group denominated as "Birds Nest" types based on its origin. The new variety presents an average of 9 leaves per plant when it reaches its maturity (between 3-4 months from rooted liner).

The new variety is moderately drought tolerant and adapts well to conditions of bright light as well as heavy shade (exterior and interior). Under high shade levels the contrast of the variegation pattern reduces substantially.

The leaves show a variegated coloration, with a central wide band of darker green and a border of lighter yellowish-green. The whole leaf is horizontally traversed by alternate bands of darker green (as characteristic of and typically seen in many *Sansevieria trifasciata* cultivars).

The central broad green band shows green colorations varying from a dark green similar to Green 139A to a lighter color similar to Yellow-Green 147C or 148D. However, due to considerable variability of color shade and the overlying creamy coloration it is difficult to pin point the exact shade.

The attached color pictures are a better guide to the overall coloration (and also the leaf phyllotaxy and spatial arrangement which are the real unique elements of this plant). As such, the coloration is very similar and not in any significant way different from several similarly colored *Sansevieria* cultivars including the common, unpatented *Sansevieria trifasciata* 'Future Superba' (unpatented) and the very old, unpatented and very well-known *Sansevieria trifasciata* 'Laurentii'.

Each leaf has marginal bands that are a brighter yellow or cream and varying in width from just 3 mm to 15 mm or even wider. This marginal band, again variable in color, has little or no green overlay and so appears brighter. This creamy color is near Yellow 4B.

Superimposed on all the above are distinct lighter horizontal cross-banding (typical of broad leaved *Sansevieria trifasciata* cultivars including *Sansevieria trifasciata* 'Futuna Superba') that is more obvious over darker central and marginal bands and very faint and hardly noticeable but present across the creamy border bands.

Backside of the leaves is similarly colored with wide central green band and creamy marginal bands and the typical S. trifasciata horizontal banding.

Young shoots are similar color overall but the border bands are more light green than cream: this color is similar to Yellow-Green 144C. As the leaves mature this border gets progressively less green and more yellowish cream.

COMMERCIAL COMPARATORS

Plants of the new *Sansevieria* 'HANSOTI21' are visually closest to a substantially bigger, taller and more vertical twisted leaf unpatented cultivar from Thailand called 'Dragon Tongue' (Lin Muang Kom in Thai). While the varieties share some horticultural characteristics, plants differ substantially, as described in the characteristics in Table 1. Plants of the new *Sansevieria* 'HANSOTI21' differ from plants of the commercial cultivar 'Dragon Tongue' (unpatented) in the characteristics described in Table 1.

TABLE I

Comparison of Closest similar cultivar 'Dragon Tongue' and New variety 'HANSOTI21'

| | Characteristic | 'Dragon Tongue' | 'HANSOTI21' |
|---|---|---|---|
| 1. | Overall Plant Height | 20 to 25 cm tall | 9-10 cm tall |
| 2. | Overall Plant Width | 20 to 23 cm wide | 16 to 19 cm wide |
| 3. | Individual Leaf length | 20 to 25 cm long | 13 to 16 cm (measured along curves) |
| 4. | Individual Leaf Width | 5 to 7 cm wide | 3.5 to 7 cm wide |
| 5. | Leaf tip | Caudate with long tail 20-25 mm | Caudate with shorter tail 12-15 mm long |

Overall, the plants of 'Dragon Tongue' are taller, wider and obviously a variety that falls into the 'Compact Group' of modern *Sansevieria* cultivars but with swirling leaves forming a wide-mouthed, inverted funnel shape. In contrast, the cultivar 'HANSOTI21' presents a flat, more or less cylindrical mass of twisted leaves very suggestive of the vortex of a tornado and it falls into the 'Birds Nest Group' of modern *Sansevieria* hybrids and cultivars. FIG. 5 illustrates the distinctly different forms of these two similar yet distinctly different *Sansevieria trifasciata* cultivars.

Individual leaves of 'HANSOTI21' are much shorter, more twisted and the whole rosette is more compact and shorter. FIG. 6 illustrates these differences of individual leaves.

In terms of overall coloration and variegation pattern the variety 'HANSOTI21' looks similar to the Cultivar 'Dragon Tongue' and other similarly colored cultivars such as 'Futuna Superba'. There is nothing distinctive in the coloration and similar coloration is typically seen in several other *Sansevieria trifasciata* cultivars. It is the plant form—the swirling pattern of its leaves forming a 'vortex' and low height/flat presentation that are the main distinctive characteristics of 'HANSOTI21'.

PARENTAL COMPARISON

Plants of the new *Sansevieria* 'HANSOTI21' differ from plants of the parental cultivar in the characteristics described in Table 2.

TABLE 2

Comparison of New and Parental variety

| | Characteristic | Parent 'Hahnii Green Compacta' | 'HANSOTI21' |
|---|---|---|---|
| 1. | Overall Color | Green striated | Wide green striated center with a creamy yellow border. |
| 2. | Border | Yellow border 3 to 15 mm | Bright green border 1 to 15 mm |
| 3. | Leaf aspect | Slightly arched and slightly to moderately undulating | Twisted and curved |
| 4. | Leaf Arrangement | Rosette, upright | Flat spiral rosette |

BRIEF DESCRIPTION OF THE PHOTOGRAPHS

The accompanying photographs illustrate the overall appearance of the new *Sansevieria* cultivar 'HANSOTI21' showing the colors as true as is reasonably possible with colored reproductions of this type. Colors in the photographs may differ slightly from the color value cited in the detailed botanical description which accurately describe the color of 'HANSOTI21'.

These pictures illustrate the plant form which is the unique characteristic of 'Hansoti21' and at the same time demonstrates that plant coloration and variegation pattern is similar to several other *Sansevieria trifasciata* cultivars. All plants were grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions). These conditions closely approximate those used in commercial practice in India.

Figure 1:
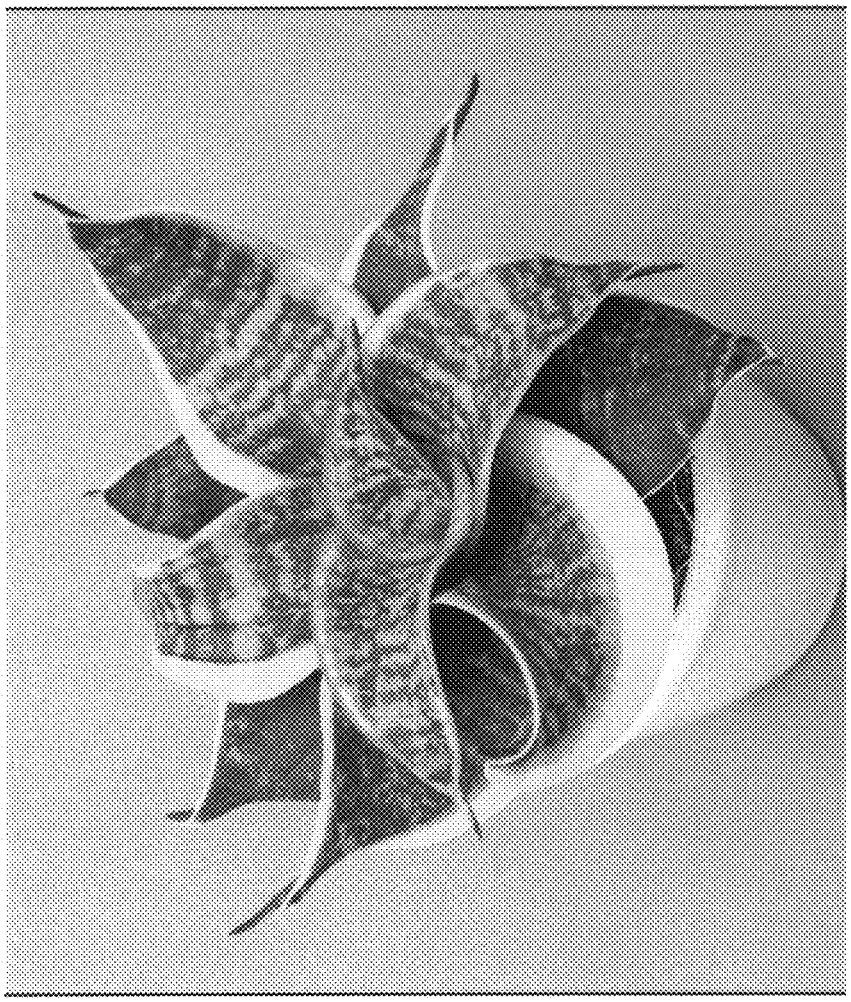
FIG. 1 shows a four-month-old plant of *Sansevieria* 'HANSOTI21' in a 12 cm diameter pot.
Figure 2:
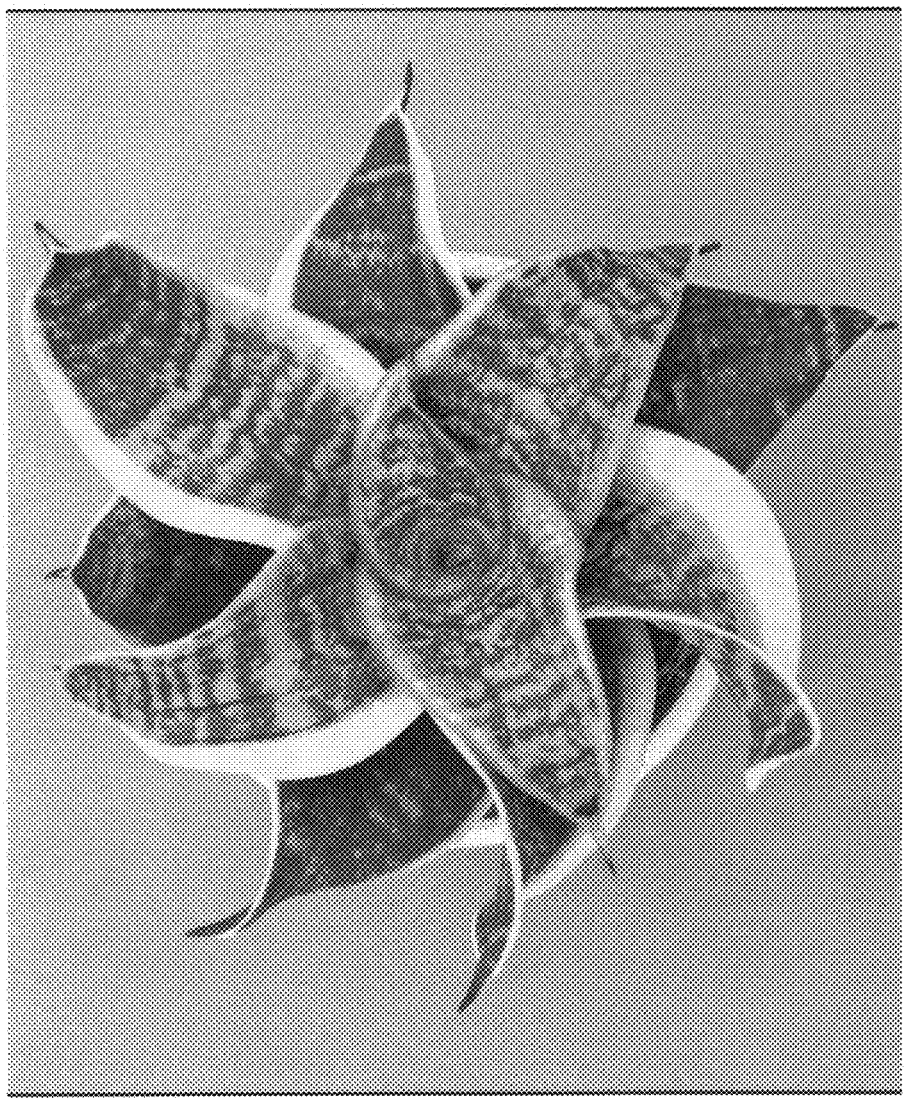
FIG. 2 shows a top view of a plant of 'HANSOTI21' showing clearly the spiral formation of the leaves.
Figure 3:
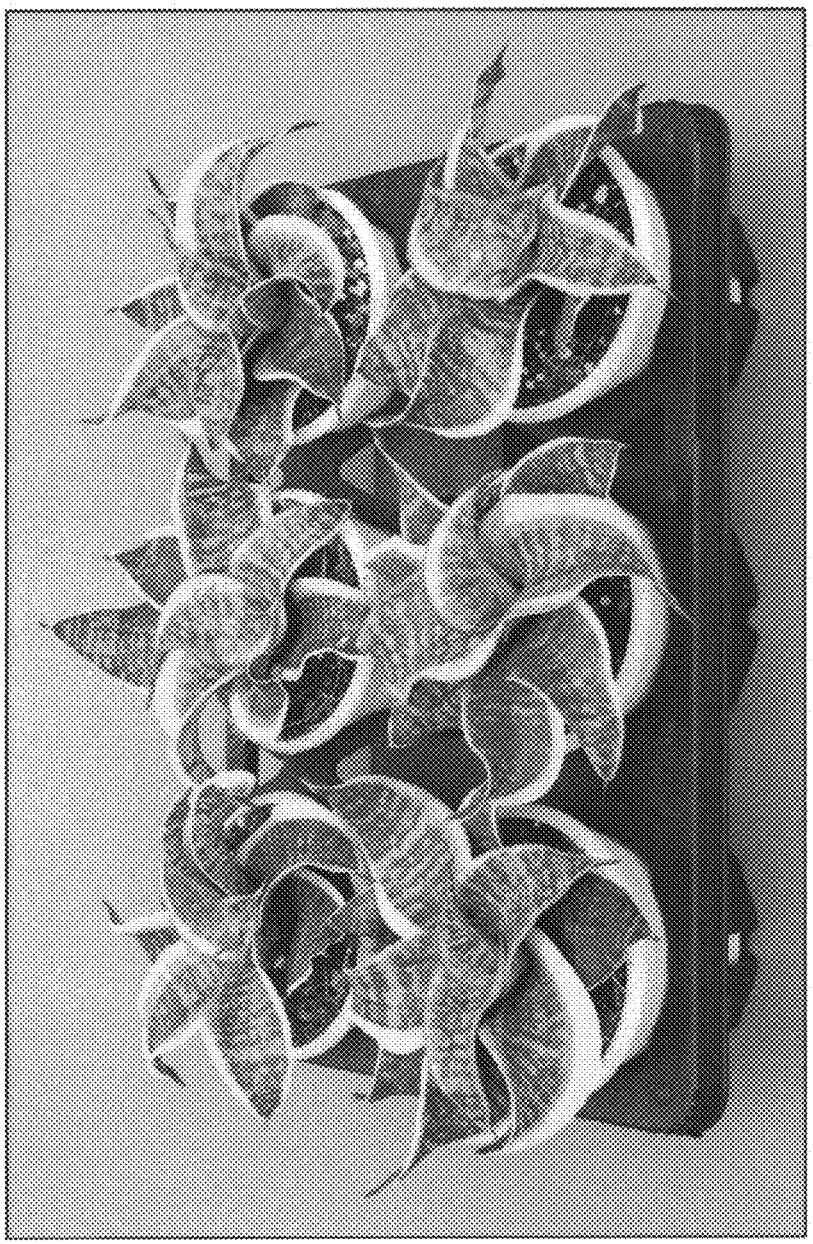
FIG. 3 shows a tray holding 6 'HANSOTI21' plants in 12 cm pots showing uniformity across multiple plants of this new cultivar.
Figure 4:
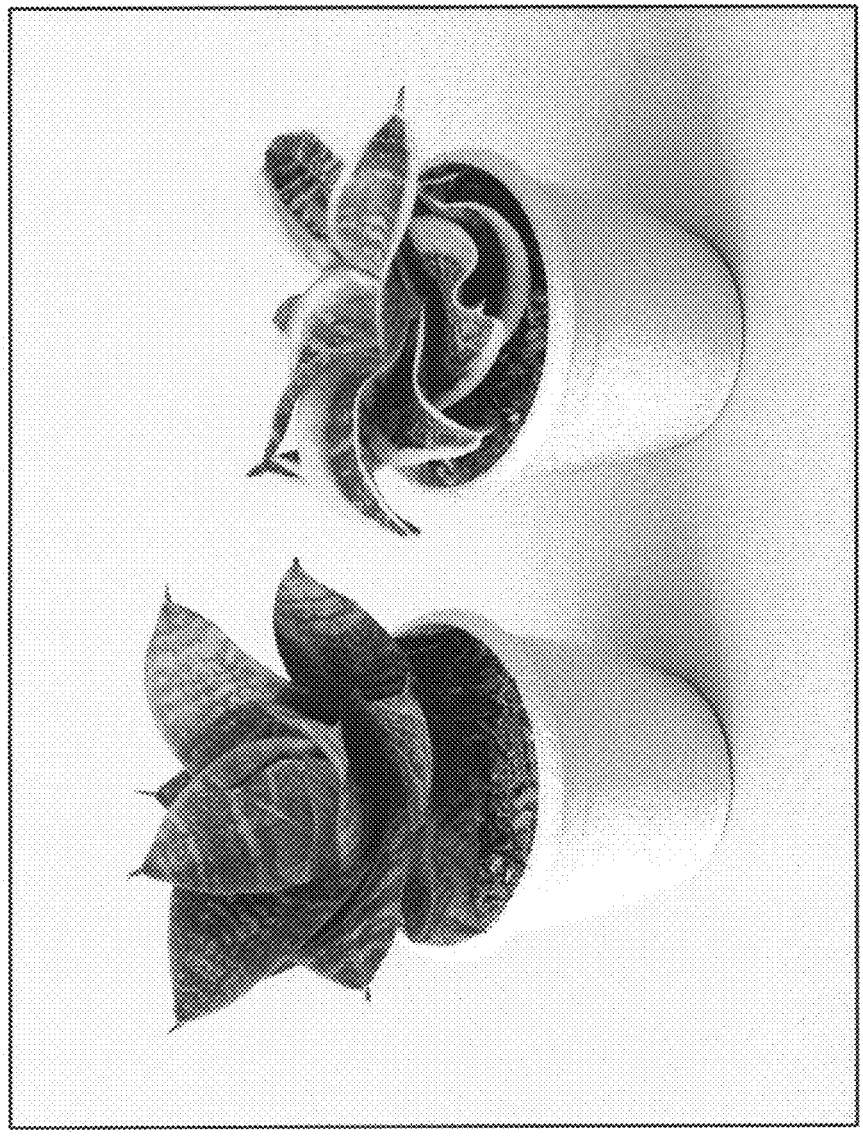

FIG. 4 shows 'HANSOTI21' besides the parent plant, *Sansevieria* 'Green Compacta'. The parent plant is on the left, the new variety on the right. Note the flattened presentation of the 'HANSOTI21' rosette even when compared to the compact parental 'Hahnii Green Compacta'.

Figure 5:
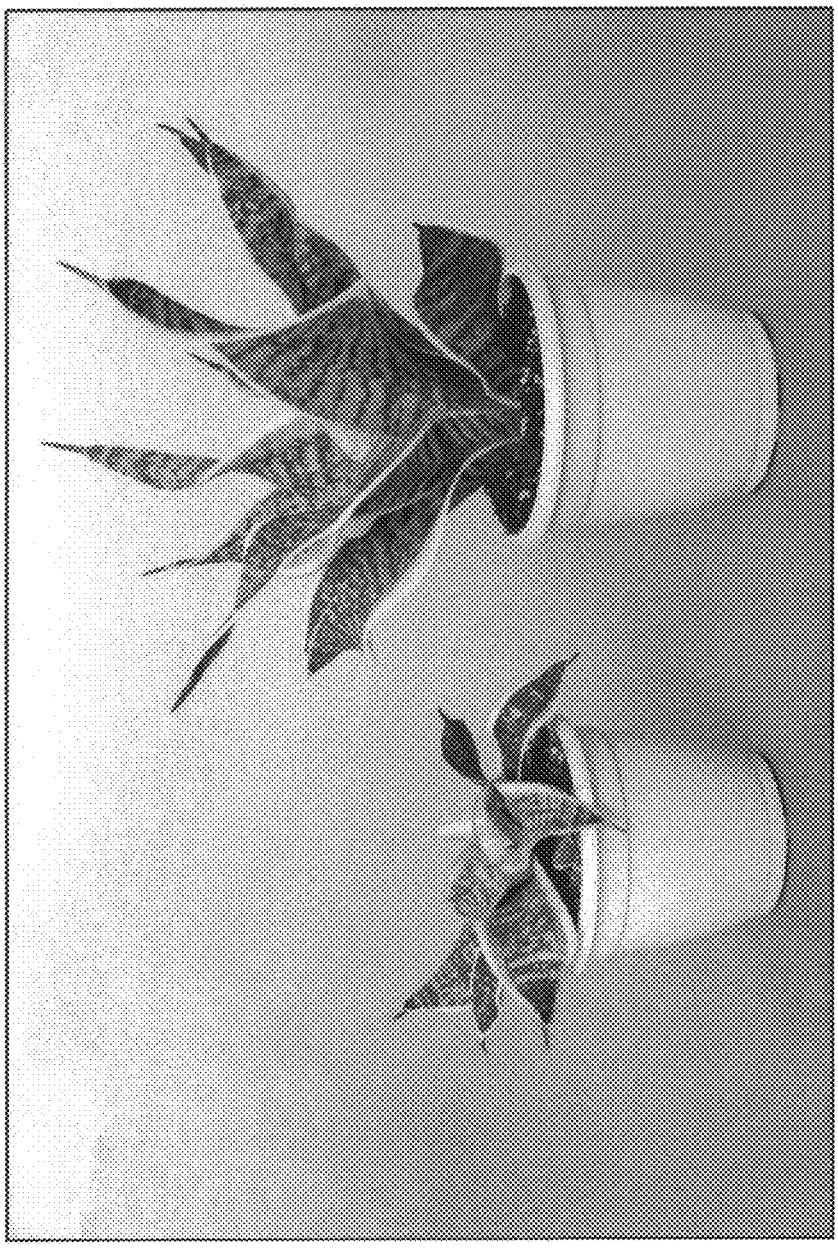

FIG. 5 shows a plant of 'HANSOTI21'(on left) in a 12 cm pot side by side with a plant of closest comparable cultivar, 'Dragon Tongue'(on right) in a 13.5 cm pot.

Figure 6:
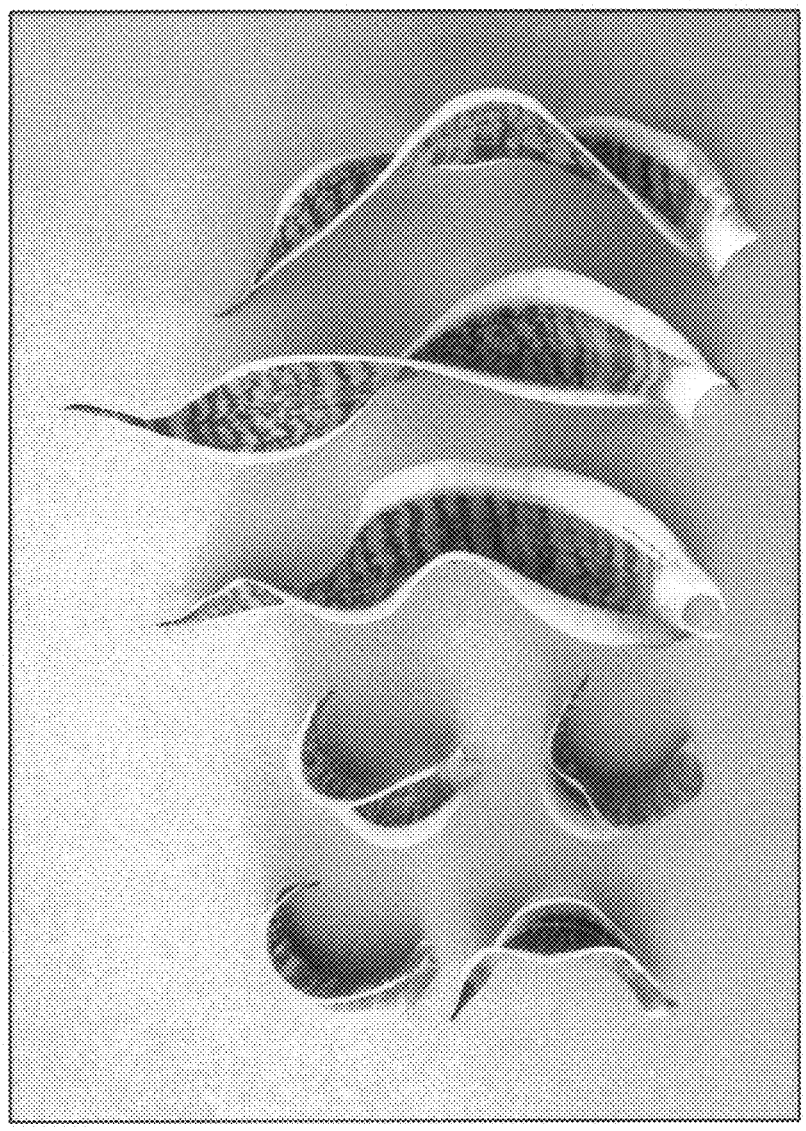

FIG. 6 shows individual leaves of *Sansevieria* 'HANSOTI21' (on left) compared to individual leaves of *Sansevieria* 'Dragon Tongue' (on right). Illustrated is the substantial difference in size and curvature pattern with 'Dragon Tongue' leaves, which are much bigger than leaves of 'HANSOTI21'.

DETAILED BOTANICAL DESCRIPTION

The new *Sansevieria* 'HANSOTI21' has not been observed under all possible environmental conditions. The phenotype of the new cultivar may vary with variations in environment such as temperature, light intensity, fertilizer levels and composition and day length without any change in the genotype of the plant.

The aforementioned photographs, together with the following observations, measurements and values describe the new *Sansevieria* cultivar 'HANSOTI21' plants grown in an open poly house (high tunnel) at Village Asle, District Satara, Maharashtra State in Western India. Average temperature in Asle is 25° C. with summer highs of 39° C. and winter lows of 6° C. Plants grow under natural light conditions and between 30% to 75% shade levels depending on the season (higher shade in hot summer conditions).

This crop gets nearly constant fertilization to increase production Constant Liquid Feed at approximately 150 ppm N, 30 ppm P and 150 ppm K is used along with micronutrients. Production is closely related with proper and complete plant nutrition and an open soilless growing media based on coconut coir. The plants are grown in plastic pots on metal benching in spacing trays Color references are made to The Royal Horticultural Society Colour Chart (R.H.S.), (April 2009) except where general colors of ordinary significance are used.

The photographs and descriptions were taken during the Winter season in Asle, District Satara, Maharashtra State, India when outdoor day temperature was 25° C. to 30° C. The age of the plants described is 3-4 months.

Botanical classification: *Sansevieria trifasciata* 'HANSOTI21'.

General information:

*Parentage.*—*Sansevieria trifasciata* 'Hahnii Green Compacta' (unpatented).

*Optimal growth conditions.*—

*Light intensities.*—High adaptability to outdoor or indoor conditions.

*Temperature.*—Day: 25° C. to 35° C. Night: 12° C. to 25° C.

*Temperature tolerance.*—Tolerant to a low temperature of about 8° C. and a high temperature of 38° C. and above — very heat tolerant.

*Fertilization.*—Constant feed of 150 ppm N, 30 ppm P and 150 ppm K is used along with micronutrients with occasional leaching.

*Growth regulators.*—Not necessary for growth, however rooting hormone aids in rapid and prolific rooting of offsets.

Propagation:

*Typical.*—Side suckers which come true to type.

*Rooting habit and description.*—Rhizomes are elongated, fleshy, giving rise to offsets (side shoots). Offsets root easily with fibrous adventitious roots from cut end. Colored cream to brown, not accurately measured with R.H.S. chart.

*Time to initiate roots.*—15 to 20 days at 25 to 30° C.

*Time to produce a rooted liner.*—About 45 days at 25° C. to 30° C.

*Time to produce ready* 12 *cm potted plant from liner.*—About 3 months at 25° C. to 30° C.

Plant:

*General appearance and form.*—Flattened, twisting rosette.

*Height.*—About 10 cm when grown in 12 cm pots.

*Spread.*—About 15 to 21 cm when grown when grown in a 12 cm size container.

*Form.*—Monocot; leaf bases arranged in a rosette around growth point.

*Shape.*—Flat cylindrical.

Foliage:

*Quantity.*—About 7 to 10 in ready to sell plant. Number slowly increases with age and rosette increases in height.

*Arrangement and attachment.*—Single, alternate; leaf bases arranged in a twisting rosette around central growth point.

*Leaf length.*—About 14 to 17 cm, full mature leaf.

*Leaf width.*—About 3.5 cm to 6 cm, full mature leaf.

*Overall shape of leaf.*—Lanceolate.

*Aspect.*—Twisted and curved.

*Apex shape.*—Acute, aristate soft tip.

*Base shape.*—Truncate.

*Margin.*—Entire. Sharp, smooth.

*Texture.*—Upper Surface: smooth and waxy texture.

*Texture.*—Under Surface: smooth and waxy texture.

*Pubescence.*—None.

*Color of mature leaf.*—Upper Surface: Near RHS Green 139A, Yellow-Green 147C and 148B, colors present as crossbands.

*Color of mature leaf.*—Lower Surface: Near RHS Green 139A, 139B, Yellow-Green 147C and 148B, colors present as crossbands.

*Margin coloration.*—Near RHS Yellow 4A and 4B.

*Venation.*—Pattern: Longitudinal/parallel leaf shape.

*Venation color.*—Indistinguishable from leaf blade.

*Leaf fragrance.*—None.

Other:

*Inflorescence description.*—Flowers not observed to date.

*Weather resistance.*—Moderately drought tolerant.

*Pest resistance.*—Reasonably resistant to pests, susceptible to root mealybugs (*Rhizoecus pritchardi*). Typical pets include *Pseudococcidae longispinus* and *Tetranychus urticae.*

*Disease resistance.*—Occasionally shows Anthracnose and leaf spots but largely disease free from clean mother stock.

*Fruit/seed production.*—No fruits/seeds detected to date.

What is claimed is:

1. A new and distinct cultivar of *Sansevieria* plant named 'HANSOTI21' as herein illustrated and described.

* * * * *